US00PP13011P2

(12) United States Plant Patent
van Tol

(10) Patent No.: US PP13,011 P2
(45) Date of Patent: Sep. 24, 2002

(54) DELPHINIUM PLANT NAMED 'DARWIN'S BLUE INDULGENCE'

(75) Inventor: Benjamin Roelof van Tol, Abbenes (NL)

(73) Assignee: Witteman + Co. 'Multiflora' B.V., Hillegom (NL)

( * ) Notice: Subject to any disclaimer, the term of this patent is extended or adjusted under 35 U.S.C. 154(b) by 2 days.

(21) Appl. No.: 09/838,943

(22) Filed: Apr. 23, 2001

(51) Int. Cl.[7] ..... A01H 5/00
(52) U.S. Cl. ..... Plt./263
(58) Field of Search ..... Plt./263

(56) References Cited

PUBLICATIONS

UPOV ROM GTITM Computer Database 2001/06, GTI Jouve Retrieval Software, Citation for 'Darwin's Blue Indulgence'.*

* cited by examiner

*Primary Examiner*—Bruce R. Campell
*Assistant Examiner*—W C Baker
(74) *Attorney, Agent, or Firm*—C. A. Whealy

(57) ABSTRACT

A distinct cultivar of Delphinium plant name 'Darwin's Blue Indulgence', characterized by its upright plant habit; freely flowering habit; and double blue-colored flowers.

2 Drawing Sheets

BOTANICAL CLASSIFICATION

*Delphinium elatum.*

BACKGROUND OF THE INVENTION

The present Invention relates to a new and distinct cultivar of Delphinium plant, botanically known as *Delphinium elatum,* and hereinafter referred to by the name 'Darwin's Blue Indulgence'.

The new Delphinium was discovered by the Inventor in a controlled environment in Abbenes, The Netherlands, as a naturally-occurring mutation of an unidentified selection of *Delphinium elatum.* The new Delphinium was selected by the Inventor on the basis of its double blue-colored flowers.

Asexual reproduction of the new cultivar by cuttings in a controlled environment in Hillegom, The Netherlands, since 1999, has shown that the unique features of this new Delphinium are stable and reproduced true to type in successive generations.

SUMMARY OF THE INVENTION

Plants of the cultivar Darwin's Blue Indulgence have not been observed under all possible environmental conditions. The phenotype may vary somewhat with variations in environment such as temperature, light intensity, daylength, irrigation amount and frequency, and/or fertilizer type or rate without, however, any variance in genotype.

The following traits have been repeatedly observed and are determined to be the unique characteristics of 'Darwin's Blue Indulgence'. These characteristics in combination distinguish 'Darwin's Blue Indulgence' as a new and distinct cultivar:

1. Upright plant habit.
2. Freely flowering habit.
3. Double blue-colored flowers.

Plants of the cultivar Darwin's Blue Indulgence differ from the parent selection and other known cultivars of Delphinium in its double flower form and flower color.

BRIEF DESCRIPTION OF THE PHOTOGRAPHS

The accompanying colored photographs illustrate the overall appearance of the new Delphinium, showing the colors as true as it is reasonably possible to obtain in colored reproductions of this type. Colors in the photographs may differ slightly from the color values cited in the detailed botanical description which accurately describe the colors of the new Delphinium.

The photograph on the first sheet comprises a side perspective view of a typical flowering plant of 'Darwin's Blue Indulgence'.

The photograph at the top of the second sheet is a close-up view of typical flowers of 'Darwin's Blue Indulgence'.

The photograph at the bottom of the second sheet is a close-up view of the upper surface of a typical leaf of 'Darwin's Blue Indulgence'.

DETAILED BOTANICAL DESCRIPTION

In the following description, color references are made to The Royal Horticultural Society Colour Chart except where general terms of ordinary dictionary significance are used. Plants used for the photographs and the following description were about 30 weeks old and grown under field conditions which closely approximate commericial production conditions during the spring and summer in Hillegom, The Netherlands.

Botanical classification: *Delphinium elatum* cultivar Darwin's Blue Indulgence.

Parentage: Naturally-occurring mutation of an unidentified selection of *Delphinium elatum,* not patented.

Propagation:

*Type cutting.*—By cuttings.

*Time to initiate roots.*—About 14 days at 14° C.

*Time to produce a rooted cutting.*—About40 days at 20° C.

*Root description.*—Fine.

Plant description:

*Form*.—Upright perennial flowering plant with double flowers arranged on erect racemes. During a growing season, about five flower racemes develop per plant.

*Crop time*.—After rooting, about 30 weeks are required to produce finished flowering plants in 2-liter containers.

*Plant height*.—About 120 cm.

*Plant diameter*.—About 40 cm.

*Vigor*.—Vigorous.

*Flowering stems*.—Length: About 50 cm. Diameter: About 3 mm. Internode length: About 3 cm. Texture: Smooth, slightly glaucous. Color: 138B to 139C.

*Foliage description*.—Leaves simple, generally symmetrical, and long-persisting. Arrangement: Rosette at the base and alternate along flowering stems. Length: About 18 cm. Width: About 25 cm. Shape: Deeply palmately to pedately-lobed. Apex: Acute. Base: Attenuate. Margin: Incised to laciniate. Texture: Upper surface: Glabrous. Lower surface: Sparsely pubescent at veins and margins. Venation pattern: Laciniate. Color: Young foliage, upper surface: 143A. Young foliage, lower surface: 138B. Fully expanded foliage, upper surface: 137A; venation, 143A. Fully expanded foliage, lower surface: 138B; venation, 143A. Petiole: Length: About 13 cm. Diameter: About 4 by 5 mm. Texture: Smooth. Color: 143A.

Flower description:

*Appearance*.—Numerous, double flowers arranged in racemes; zygomorphic. Flowers not persistent.

*Quantity of flowers*.—Freely flowering. Primary or main flowering stem, about 65 flowers; secondary flowering stems, about 25 flowers each.

*Natural flowering season*.—Late summer in The Netherlands; flowering continuous during this period.

*Fragrance*.—Not fragrant.

*Flower longevity on the plant*.—About 10 to 14 days.

*Flower longevity as a cut flower*.—At least 10 days.

*Flower size*.—Diameter: About 6.5 cm. Depth, excluding spur: About 1.7 cm.

*Flower buds*.—Length, excluding spur: About 1.7 cm. Diameter: About 1.1 cm. Shape: Ovoid. Color: 143B to 143C with 115D overtones.

*Petals/petaloids*.—Appearance/arrangement: About 5 petals and about 18 petaloids per flower arranged in multiple whorls. Length: Petals: About 3.7 cm. Petaloids, largest: About 3.5 cm. Width: Petals: About 2.4 cm. Petaloids, largest: About 1.7 cm. Shape: Petals: Elliptic to broadly elliptic. Petaloids: Outer petaloids: Elliptic. Innermost petaloids: Flabellate to spatulate. Apex: Petals: Acute to abruptly acute. Petaloids: Acute to rounded. Margin: Entire: Texture: Petals: Smooth. Petaloids: Sparsely pubescent towards the base. Color: Petals: When opening, upper surface: 101B to 104C. When opening, lower surface: 101C, with a green, 143A to 143B, spot towards the petal apex. Fully opened, upper surface: 101B to 104B. Fully opened, lower surface: 97A to 104C, with a green, 143A to 143B, spot towards the apex. Petaloids: Immature, both surfaces: Between 98C to 98D to 100C; random white, 155D, areas towards the apex. Mature, both surfaces: 104C; random white, 155D, areas towards the apex. Spur: Arrangement: On uppermost outer petal, downwardly bending. Length: About 1.8 cm. Diameter: About 1 mm. Color: 92B to 97B.

*Sepals*.—Appearance/arrangement: Two per flower; opposite. Calyx length: About 1.1 cm. Calyx diameter: About 6 mm. Shape: Linear. Apex: Acuminate. Margin: Entire. Texture: Sparsely pubescent. Color: Upper surface: 143A to 143B. Lower surface: 143A.

*Pedicel*.—Length: About 6 cm. Angle: About 30° from vertical. Strength: Strong. Texture: Smooth. Color: 137A to 141A.

*Reproductive organs*.—Stamens: Quantity: About 25 per flower. Anther length: About 1 mm. Anther shape: Reniform. Anther color: 200B. Pollen amount: Scarce. Color: Pale creamy white, close to 158A. Pistils: Quantity: Six per flower. Pistil length: About 2 mm. Stigma shape: Two-parted. Stigma color: Whitish purple. Style length: About 2 mm. Style color: 91A to 91B. Ovary color: 141C to 143C.

*Seed description*.—Shape: Roughly spherical. Length: About 1.5 mm. Diameter: About 1.5 mm. Color: 200A to 202A.

Disease resistance: Plants of the new Delphinium have not been noted to be resistant to pathogens common to Delphinium.

It is claimed:

1. A new and distinct cultivar of Delphinium plant named 'Darwin's Blue Indulgence', as illustrated and described.

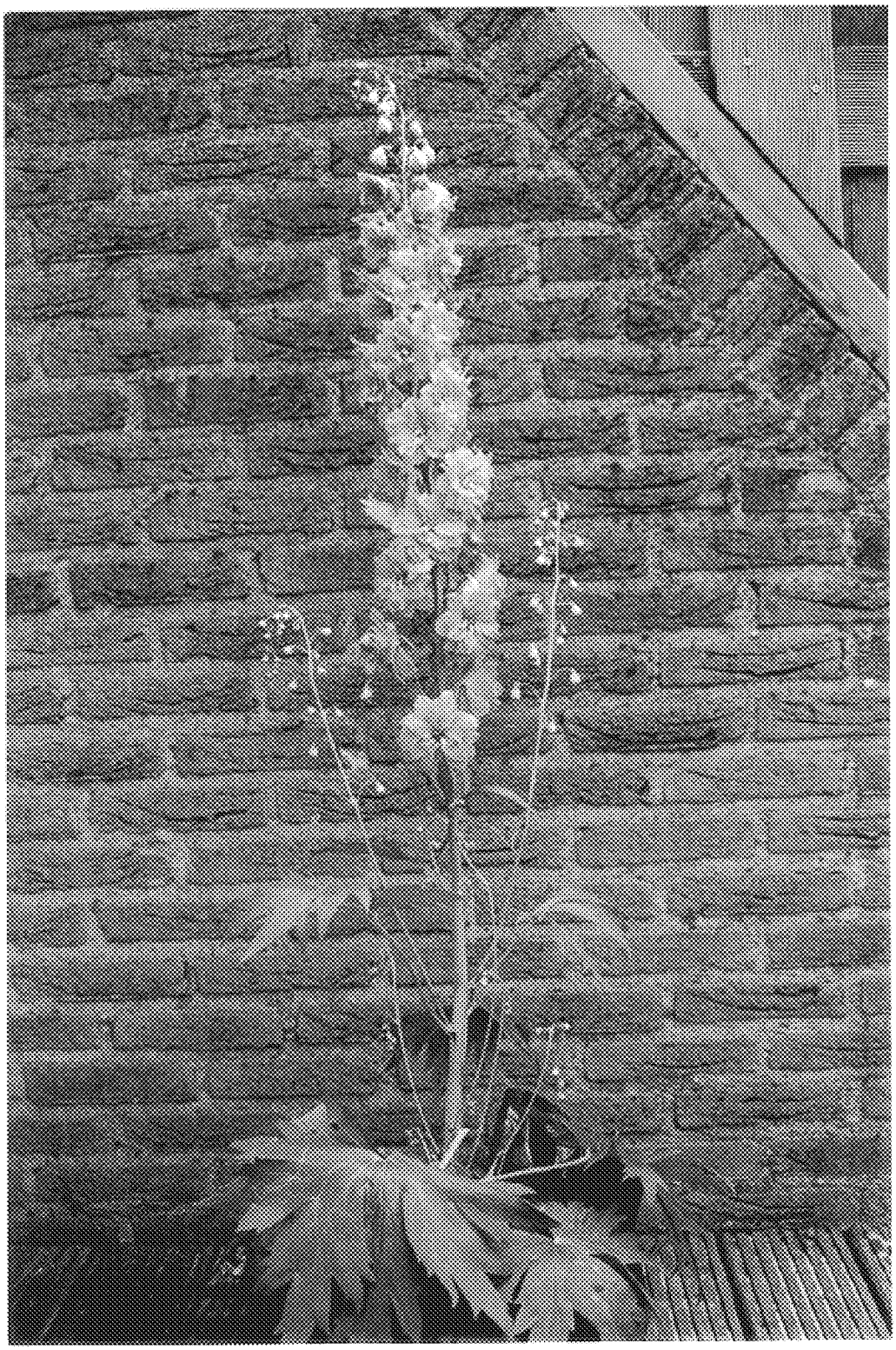

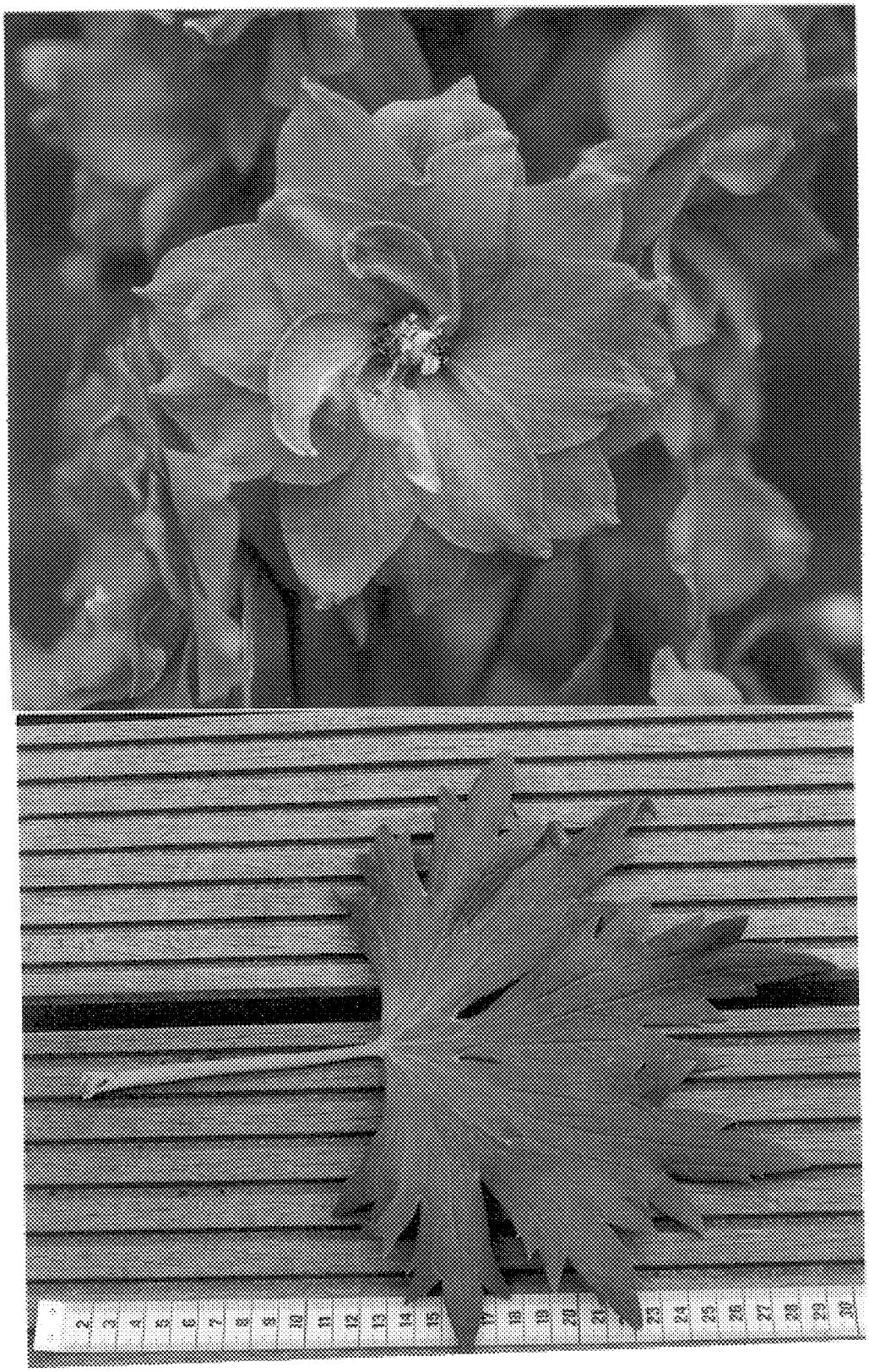

* * * * *